(12) United States Patent
Popovic et al.

(10) Patent No.: US 10,506,930 B2
(45) Date of Patent: Dec. 17, 2019

(54) MICROWAVE THERMOMETER FOR INTERNAL BODY TEMPERATURE RETRIEVAL

(71) Applicant: THE REGENTS OF THE UNIVERSITY OF COLORADO, Denver, CO (US)

(72) Inventors: Zorana Popovic, Boulder, CO (US); Robert Scheeler, Boulder, CO (US); Parisa Momenroodaki, Boulder, CO (US); William David Haines, Boulder, CO (US)

(73) Assignee: The University of Colorado, a body corporate, Denver, CO (US)

( * ) Notice: Subject to any disclaimer, the term of this patent is extended or adjusted under 35 U.S.C. 154(b) by 298 days.

(21) Appl. No.: 15/608,284

(22) Filed: May 30, 2017

(65) Prior Publication Data

US 2017/0340208 A1 Nov. 30, 2017

Related U.S. Application Data

(60) Provisional application No. 62/342,762, filed on May 27, 2016.

(51) Int. Cl.
*G01J 5/00* (2006.01)
*G01K 7/00* (2006.01)
(Continued)

(52) U.S. Cl.
CPC .............. *A61B 5/01* (2013.01); *A61B 5/0507* (2013.01); *A61B 5/6833* (2013.01); *G01B 15/02* (2013.01); *G01K 11/006* (2013.01); *G01K 13/002* (2013.01); *A61B 2560/0412* (2013.01); *A61B 2562/0228* (2013.01); *A61B 2562/0271* (2013.01)

(58) Field of Classification Search
USPC ......................................... 374/122, 179, 208
See application file for complete search history.

(56) References Cited

U.S. PATENT DOCUMENTS 5,149,198 A * 9/1992 Sterzer ................. G01K 11/006
374/122
5,176,146 A * 1/1993 Chive ...................... A61N 5/02
600/549

(Continued)

*Primary Examiner* — Mirellys Jagan
(74) *Attorney, Agent, or Firm* — Holzer Patel Drennan

(57) ABSTRACT

Systems and methods are described for microwave-frequency, passive sensing of internal body temperature. Some implementations include one or more wearable sensors that wirelessly transmit temperature data continuously to a remote receiver. The sensor can include a probe designed to be placed on a skin site of an individual to receive near-field radiation at the skin site, and a radiometer to detect a total power of the received near-field radiation. The remote receiver includes a signal processing system that can convert the detected total power to an internal tissue temperature measurement by applying the detected power to a tissue stack model. The tissue stack model can characterize the skin site according to a set of weighting functions, each weighting function corresponding at least to electromagnetic characteristics of an associated tissue layer of the tissue stack model.

17 Claims, 6 Drawing Sheets

(51) Int. Cl.
*G01K 1/00* (2006.01)
*A61B 5/01* (2006.01)
*G01B 15/02* (2006.01)
*G01K 11/00* (2006.01)
*A61B 5/05* (2006.01)
*A61B 5/00* (2006.01)
*G01K 13/00* (2006.01)

(56) References Cited

U.S. PATENT DOCUMENTS

| | | | | |
|---|---|---|---|---|
| 2002/0190815 | A1* | 12/2002 | Takamine | H03H 9/02834 333/195 |
| 2009/0187115 | A1* | 7/2009 | Yarden | A61B 5/01 600/549 |
| 2018/0058945 | A1* | 3/2018 | Vesnin | G01K 11/006 |

* cited by examiner

MICROWAVE THERMOMETER FOR INTERNAL BODY TEMPERATURE RETRIEVAL

GOVERNMENT RIGHTS STATEMENT

This invention was made with government support under grant number ECCS1202193 awarded by the National Science Foundation. The government has certain rights in the invention.

FIELD

Embodiments relate to wearable sensors, and, more particularly, to portable microwave thermometers for internal body temperature retrieval.

BACKGROUND

There are a number of health-related applications that benefit from knowledge (e.g., periodic and/or constant monitoring of) of core body temperature. Generally, the external temperature of a human body can differ from the temperature of internal tissues of a human body by as much as 2.5 degrees Kelvin, and can also vary during the day (e.g., as a natural physiological process, in relation to exercise, in relation to eating, etc.). A number of disorders can cause this temperature difference can vary from that in a healthy body. For example, athletes, soldiers, firefighters and other professions working in extreme conditions or under heavy exertion can experience exertional hyperthermia. Such hyperthermia can result in fatigue, heat-related illness, and even death. Cancer cells can have increased temperatures, as can inflamed tissues, such as those in joints of arthritis patients. Sleeping disorders are accompanied by changes in the circadian cycle, which can also be related to changes in phase and amplitude of periodic variations in core body temperature. Infants suffering from hypoxia-ischemia have an elevated brain temperature; and, if detected, can be effectively treated.

Thus, internal temperature monitoring can be used in various diagnostics applications, for example, as an indication of one or more disorders or conditions. Further, some treatments for such disorders and conditions (e.g. in hyperthermia for cancer treatment) can be aided by internal temperature monitoring. A number of techniques exist for monitoring core body temperature. Most conventional techniques tend to involve invasive methods, such as rectal probes, gastro-intestinal sensors, surgically inserted thermometers, etc. Some other conventional techniques are less invasive or non-invasive. For example, some approaches use zero-heat-flux sensing techniques. However, it has been generally accepted that no non-invasive methods are currently considered acceptable for diagnosing heat-related illness.

BRIEF SUMMARY

Among other things, systems and methods are described for microwave-frequency, passive sensing of internal body temperature. Some embodiments include techniques for calibration and processing of the internal body temperature sensing. For example, implementations can retrieve temperature changes internal to the body and at depths of several centimeters with a resolution of a fraction-of-a-degree Kelvin. In one embodiment, a portable (e.g., small, wearable) sensor can wirelessly transmit temperature data continuously to a remote receiver, where much of the signal processing can be performed. For example, the sensor includes a probe and a radiometer. The probe is designed to be placed on a skin site of an individual, the probe operable to receive near-field radiation at the skin site. The radiometer operates to detect a total power of the received near-field radiation. The remote receiver includes a signal processing system that can convert the detected total power to an internal tissue temperature measurement by applying the detected power to a tissue stack model. The tissue stack model can characterize the skin site according to a set of weighting functions, each weighting function corresponding at least to electromagnetic characteristics of an associated tissue layer of the tissue stack model.

BRIEF DESCRIPTION OF THE DRAWINGS

The present disclosure is described in conjunction with the appended figures.

Figure 1:
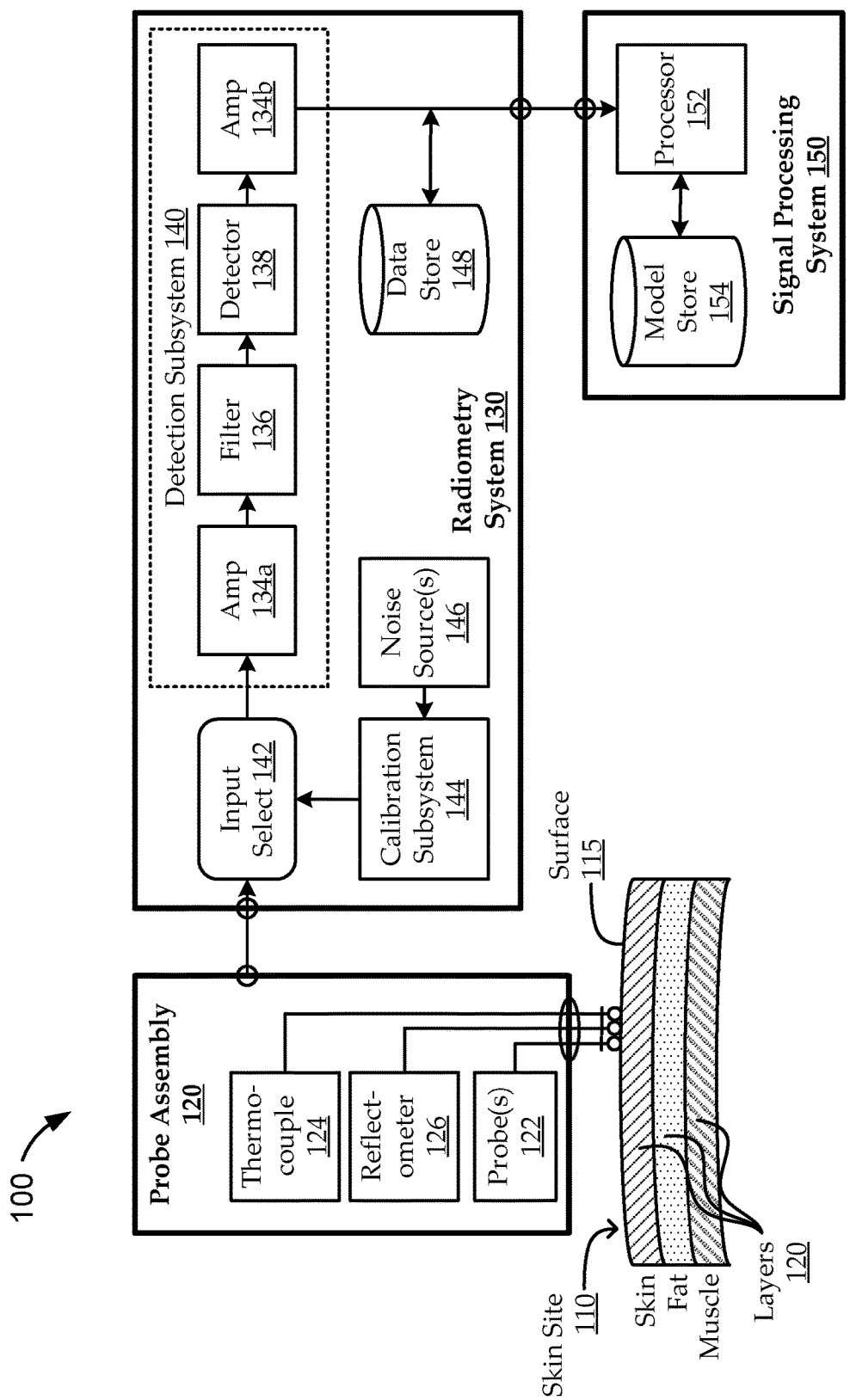
FIG. 1 shows a block diagram of an illustrative core body temperature-monitoring environment, according to various embodiments.

In the appended figures, similar components and/or features can have the same reference label. Further, various components of the same type can be distinguished by following the reference label by a second label that distinguishes among the similar components. If only the first reference label is used in the specification, the description is applicable to any one of the similar components having the same first reference label irrespective of the second reference label.

DETAILED DESCRIPTION

Many health-related diagnostic and therapeutic applications can benefit from knowledge (e.g., periodic and/or constant monitoring of) of core body temperature. As used herein, "core" temperature generally refers to any internal body temperature (e.g., temperature of internal tissue layers, as opposed to surface body temperature) at any depth. Generally, the external temperature of a human body can differ from the temperature of internal tissues of a human body by as much as 2.5 degrees Kelvin, and can also vary during the day (e.g., as a natural physiological process, in relation to exercise, in relation to eating, etc.). In a number of disorders, this temperature difference can vary from that in a healthy body.

A number of techniques exist for monitoring core body temperature, including invasive and non-invasive techniques. Generally, conventional non-invasive techniques, such as zero-heat-flux sensing techniques, have been considered unacceptable for diagnosing heat-related illness.

Accordingly, most conventional techniques tend to involve invasive methods, such as rectal probes, gastro-intestinal sensors, surgically inserted thermometers, etc. Some such conventional technique uses an ingestible sensors (e.g., a pill) having a short-range wireless device that can measure the temperature somewhere in the digestive track for a limited time while the device is in the body. Such ingestible sensors tend to be unpleasant to administer (e.g., large, hard to swallow, etc.), single-use, short-term (e.g., only remaining in the digestive track for one or two days), difficult to locate (e.g., it can be difficult to know where the sensor is at any time), etc. Other such conventional techniques use Magnetic Resonance Imaging (MRI). MRI-based approaches can measure temperature distribution with high spatial resolution, but they tend to be very expensive and not portable. Some other such conventional techniques use microwave core-body thermometry (e.g., mostly limited to infant brain temperature measurements and monitoring of astronaut temperature in space-suits). In these cases, the environment is typically shielded, or relatively large shielded probes are used, such that the technique has not been effectively applied in real-world (e.g., wearable device, unshielded, etc.) contexts. Thus, the above and other conventional approaches are not typically conducive to diagnostic and therapeutic contexts that prefer (or require) continuous temperature monitoring, portability (e.g., implementation as a wearable device), etc.

Embodiments described herein include methods and systems for microwave-frequency, passive sensing of internal body temperature. Some implementations can include appropriate signal processing algorithms and system calibration, and some can retrieve temperature changes internal to the body and at depths of several centimeters with a resolution of a fraction-of-a-degree Kelvin. Some embodiments can be implemented as a portable (e.g., small, wearable) sensor that can wirelessly transmit temperature data continuously to a remote receiver, where much of the signal processing can be performed. Such implementations can be applied to health monitoring of athletes and other people under heavy training (e.g. soldiers); sleep studies and sleep disorder treatment; kidney disorder monitoring; brain temperature monitoring; temperature monitoring during various surgical treatments such as tumor ablation, blood vessel cauterization, hyperthermia, etc.; monitoring internal temperature of transplant organs during transport; monitoring internal food temperature on a production line; and/or other applications.

In the following description, numerous specific details are set forth to provide a thorough understanding of the present invention. However, one having ordinary skill in the art should recognize that the invention can be practiced without these specific details. In some instances, circuits, structures, and techniques have not been shown in detail to avoid obscuring the present invention.

FIG. 1 shows a block diagram of an illustrative core body temperature-monitoring environment 100, according to various embodiments. The core body temperature-monitoring environment 100 includes a thermometry system having a probe assembly 120, a radiometry system 130, and a signal processing system 150. For the sake of context, the probe assembly 120 is illustrated in contact with the surface 115 of a skin site 110. The skin site 110 can be any suitable location on the body of a person or other living organism. The skin site 110 can include multiple layers 120, which are illustrated in simplified form as a skin layer, a fat layer, and a muscle layer. In reality, there can be multiple sub-layers in the illustrated layers 120 (e.g., multiple layers of skin in the skin layer), and additional layers 120 (e.g., internal organs, etc.) that are not shown. Embodiments can generally be designed (e.g., by choice of operating frequencies, biomechanical and other calibration models, etc.) to measure internal temperature at one or more desired depths. For the sake of simplicity, descriptions herein assume that measurements of the muscle layer are desired as an indication of core body temperature.

As illustrated, the probe assembly 120 is coupled with the radiometry system 130, which is coupled with the signal processing system 150. Embodiments of the probe assembly 120 operate, when placed in contact with the skin site 110, to receive near-field radiation at the skin site 110. Embodiments of the radiometry system 130 can detect a total power of the near-field radiation received by the probe assembly 120. Embodiments of the signal processing system 150 can convert the detected total power to an internal tissue temperature measurement as a function of applying the detected total power to a tissue stack model. As described herein, the tissue stack model can characterize the skin site 110 according to a set of weighting functions, each corresponding at least to electromagnetic characteristics of an associated tissue layer of the tissue stack model. For example, each layer 120 of the skin site 110 can correspond to a tissue layer modeled in the tissue stack model.

Embodiments can be deployed in any suitable configuration. For example, some embodiments include a housing that partially or fully encloses the probe assembly 120 and the radiometry system 130 (e.g., with the probe(s) 122 connected thereto and/or integrated therein. The housing can also include a port (e.g., wired or wireless) for coupling with the signal processing system 150. For example, the housing can include a wireless transmitter in wireless communication with the signal processing system 150. Some such embodiments store the monitored core body temperature data for later retrieval by a signal processing system 150 (e.g., by plugging the housing into the signal processing system 150, by wireless direct communication with the signal processing system 150, by wireless communication with the signal processing system 150 via a public or private network, etc.). In other such embodiments, the housing can be in periodic or persistent wireless communication with the signal processing system 150. The housing can include supporting components, such as an on-board power supply (e.g., a battery, a wireless power receiver, etc.), a wireless antenna (e.g., for communication by Bluetooth, near field communication (NFC), WiFi, and/or any other suitable protocol), etc. In some other embodiments, the probe assembly 120, radiometry system 130, and signal processing system 150 can all be implemented in a single portable housing. For example, the radiometry system 130 and signal processing system 150 can be implemented in a single portable package with a power supply, and the probe assembly 120 can be in wired or wireless communication therewith. Some embodiments can be implemented with relatively inexpensive, commercially available (e.g., commercial off-the-shelf (COTS) components). Other embodiments can be fully or partially integrated on a chip. For example, the radiometry system 130 (e.g., or a portion thereof, such as the detector stage 138) can be wire-bonded or surface-mounted directly on the backside of the probe assembly 120 (e.g., or of the probe(s) 122), using the same substrate for mechanical support and electrical connection. Further, calibration components (e.g., noise sources, etc.), amplification components (e.g., one or more amplifier circuits), and/or other circuitry can be assembled onto a same substrate as the radiometry system 130, built into a same integrated circuit as the radiometry system 130, etc. Some implementations that include wireless communications use one or more techniques (e.g., time-sharing) to mitigate interference between the communications and the radiometry system 130 measurements.

As illustrated, embodiments of the probe assembly 120 can include one or more probes 122. The probe(s) 122 can be wearable probes. For example, the probe(s) 122 can be designed in small packages that include elements to assist with adhering the probe(s) 122 to the skin site 110 surface 115, avoiding excessive heating of the probe(s) 122, properly grounding the probe(s) 122, etc. In some embodiments, the probe 122 is implemented as a patch probe that can be impedance-matched to the skin site 110. In some implementations, the probe(s) 122 can operate to receive the near-field radiation at the skin site 110 at a frequency band tuned to correspond to a predetermined tissue penetration depth. For example, some implementations of the probe(s) 122 are designed for specific narrow-band, near-field operation in quiet bands that are reserved for radioastronomy use (e.g., 1.4 GHz and 2.6 GHz), and the circuitry can be designed to integrate the signal over time (e.g., as opposed to integrating over a larger bandwidth). Such operation can provide deep tissue penetration with low radiofrequency interference (RFI).

Some embodiments use multiple probes 122 for measurement diversity. For example, a first probe 122 can operate to receive the near-field radiation at the skin site at a first frequency band tuned to correspond to a predetermined first tissue penetration depth associated with a first tissue layer of the tissue stack model, and a second probe 122 can operate to receive the near-field radiation at the skin site at a second frequency band tuned to correspond to a predetermined second tissue penetration depth associated with a second tissue layer of the tissue stack model. Some embodiments include multiple probes 122 located differently with respect to the skin site 110 to provide spatial diversity in the measurement. In these and/or other embodiments having multiple probes 122, the probe(s) 122 can operate sequentially, concurrently, or in any other suitable manner.

In some embodiments, the probe assembly 120 also includes one or more thermocouples 124. The thermocouple(s) 124 can operate to retrieve a surface physical temperature measurement at the skin site 110 (e.g., concurrently with, subsequent to, or otherwise temporally related to the probe(s) 122 receiving the near-field radiation at the skin site 110). For example, temperature changes can take time to propagate through the layers 120 of the skin site 110, so that internal temperature changes measured by the probe(s) 122 may precede corresponding surface temperature changes measured by the thermocouple(s) 124. Embodiments of the signal processing system 150 can convert the detected total power to the internal tissue temperature measurement according to both the detected total power and the surface physical temperature measurement. For example, the signal processing system 150 can convert the detected total power to the internal tissue temperature measurement for a first time by applying the detected power to a tissue stack model having values for the set of weighting functions at the first time adjusted according to the surface physical temperature measurement for a second time that is subsequent to the first time.

In some embodiments, the probe assembly 120 also includes one or more reflectometers 126. The reflectometer(s) 126 can operate to retrieve a set of tissue layer thickness measurements according to time-domain reflectometry. For example, prior to applying the detected power to the tissue stack model, the signal processing system 150 can compute (e.g., or re-compute, adjust, verify, etc.) the tissue stack model according to the set of tissue layer thickness measurements. In some implementations, one or more tissue stack models is stored in a model data store 154 (e.g., included in, or otherwise accessible by, the signal processing system 150). In one such implementation, the signal processing system 150 operates to compute the tissue stack model by calibrating a stored tissue stack model according to the set of tissue layer thickness measurements. In another such implementation, the signal processing system 150 operates to compute the tissue stack model by selecting one of multiple stored tissue stack models that most closely corresponds to the set of tissue layer thickness measurements. For example, different models can be stored for different organisms, different body locations of the skin site 110 (e.g., chest, leg, etc.), different body types (e.g., athletic, obese, etc.), etc.

Embodiments of the radiometry system 130 can generally be implemented in any suitable architecture, such as a Dicke radiometer architecture. In the illustrated radiometry system 130, a signal path between the probe assembly 120 and the signal processing system 150 can include a detection subsystem 140. Some implementations of the detection subsystem 140 include a first amplifier stage 134*a* (e.g., a low-noise amplifier, or LNA), a filter stage 136 (e.g., a band-pass filter, or BFP), a detector stage 138, and a second amplifier stage 134*b* (e.g., a video amplifier). Some embodiments can achieve high signal gain with a low noise ratio with two or more amplifier stages 134 in the radiometry system 130, including the first stage 134 *a* having components with less gain (and correspondingly lower noise levels) to propagate less noise one or more subsequent amplification stages (e.g., stage 134*b*). In some implementations, the detector stage 138 is implemented as a square-law diode detector. For example, the detector stage 138 can include a Skyworks Schottky diode SMS7630-079 matched with a lumped element inductor-capacitor (LC) match (C=4.7 pF, L=15 nH).

As described below, some implementations include an input selector 142 that can select between an operational mode and a calibration mode of the radiometry system 130. In the operational mode, signals are received from the probe assembly 120 and passed to the detection subsystem 140. In the calibration mode, signals are received from a calibration subsystem 144 (e.g., and also from the probe assembly 120 in some implementations) and passed to the detection subsystem 140. The calibration system 144 can be implemented in any suitable manner for calibrating the radiometry system 130. In some embodiments, the calibration system 144 includes, or is coupled with, one or more calibration noise sources 146. For example, the calibration noise sources 146 can be selectively switched into the signal path (e.g., by the input selector 142) for calibration purposes in lieu of receiving signals from the probe assembly 120. In such embodiments, the detector stage 138 can detect the total power of the received near-field radiation; one or more noise sources 146 can outputs a predetermined power corresponding to a predetermined temperature; and the input selector 142 (e.g., a switch) can selectively couple the detector stage 138 with either the probe assembly 120 or the calibration noise source(s) 146. The signal processing system 150 can calibrate the radiometry system 130 by compensating for a gain offset that is determined, while the input selector 142 couples the detector stage 138 with the calibration noise source(s) 146, according to comparing the predetermined temperature with the internal tissue temperature measurement converted from the predetermined power. In some embodiments, the calibration noise sources 146 include a hot noise source that outputs a first predetermined power corresponding to a predetermined hot temperature, and a cold noise source that outputs a second predetermined power corresponding to a predetermined cold temperature. For example, in such implementations, the signal processing system 150 can compute a hot measurement while the input selector 142 couples the detector stage 138 with the hot noise source and can compute a cold measurement while the input selector 142 couples the detector stage 138 with the cold noise source; and the signal processing system 150 can calibrate the radiometry system 130 by fitting a correlation function to the hot measurement and the cold measurement and de-skewing the detected total power according to the correlation function.

Some conventional radiometry systems are implemented with architectures, such as those used in radioastronomy, terrestrial remote sensing, fire-monitoring, etc., in which the object being sensed is in the far field of an antenna that is receiving plane waves radiated by the object. In the core body thermometry case, however, the power radiated by the different tissue layers is received by a probe antenna (i.e., probe(s) 122) situated in the near field (i.e., on the skin surface 115). In a narrow measurement frequency bandwidth (B), the power received can be approximated by a simplified thermal (white) noise expression $P=kT_AB$, where $T_A$ is the antenna temperature. The antenna temperature depends on both the physical temperature and the probe antenna near-field directivity, which describes the power an antenna receives from a cone described by spherical angles ($\theta$, $\phi$). Thus, the power measured by the radiometry system 130 can effectively include powers radiating from the various tissue layers 120.

In some embodiments, to obtain an internal measurement, the reading can be compared against a model of the tissue stack-up to determine the temperature distribution over the layers. Some embodiments obtain such a model by using near-field weighting functions estimated from an electromagnetic simulation (e.g. by a finite-difference time-domain (FDTD) technique, a finite element model (FEM) technique, a semi-analytical technique, etc.). In some cases, a tissue stack-up model can be developed experimentally, for example, by inserting temperature probes at different depths in biological tissue and/or tissue analogues and collecting actual measurement data. In some cases, layers 120 can be externally measured using time-domain reflectometry and/or other techniques. In other cases, layers 120 can be measured non-invasively by body imaging technology, such as MRI, CAT scan, ultrasound, etc. In still other cases, the model of the tissue stack-up can be developed from (or can directly use) pre-existing body models that have been categorized by parameters such as height, weight, body-mass index, age, gender, race or similar physical or demographic parameters. With any of these or other types of models, the models and/or parameters can be entered into the device (e.g., stored in the model data store 154), so that the device can adjust the algorithms for the particular tissue stack-up. Entry of the model and/or parameters can be performed in any suitable manner, for example, by wired or wireless communication between the device and a user interface, by physical manipulation of one or more discrete circuit components (e.g., dip switches, knobs, etc.), by direct programming of a programmable circuit (e.g., an EPROM, etc.), etc. In some cases, pre-calibration can be facilitated by placing the device (e.g., one or more probes 122) in contact with one or more body locations where the tissue layer geometry beneath the device is known, or can be estimated. In this way, knowledge of the geometry and composition of the tissue layers, and knowledge of electromagnetic properties (e.g. emissivity and complex dielectric constant) and/or the known thermodynamic properties (thermal mass and thermal resistance) of each type of tissue layer, can be pre-programmed into the algorithm for resolving the tissue temperature in the layers 120. In some such cases, the pre-calibration can be sufficient, such that no additional calibration of the system relative to the body is necessary.

Embodiments can process the detected total power to derive an internal temperature measurement in various ways. In some embodiments, the radiometry system 130 includes, or is in communication with, a data store 148 that can store the detected total power at each of multiple times over a detection window. The data store 148 can include any suitable memory, such as a buffer, solid-state memory, etc. In such embodiments, the signal processing system 150 can convert the detected total power to the internal tissue temperature measurement at each of the times (e.g., or a portion of the times) by, for each time: accessing the stored detected total power for the time from the data store 148; and applying the accessed detected total power to the tissue stack model. In other embodiments, the signal processing system 150 includes one or more processors 152 in communication with one or more memory devices (e.g., part of, including, or separate from, the model data store 154). The memory devices can have, stored thereon, instructions, which when executed, cause the processor(s) 152 to convert the detected total power to the internal tissue temperature measurement as a function of applying the detected power to the tissue stack model (e.g., stored in the model data store 154).

Figure 2:
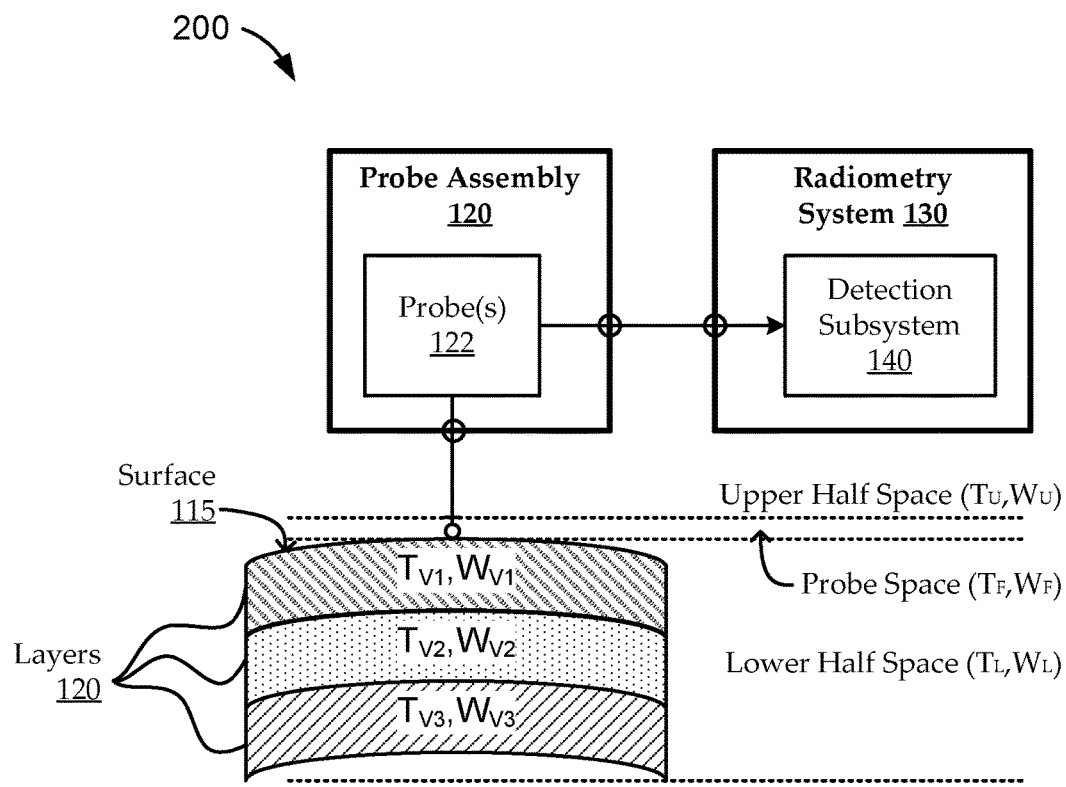
FIG. 2 shows a model of a thermometry environment with which to calculate the internal temperature from the radiometry measurements based on a tissue stack-up model.

FIG. 2 shows a model of a thermometry environment 200 with which to calculate the internal temperature from the radiometry measurements based on a tissue stack-up model. A simplified block diagram of a thermometry system is shown having a probe assembly 120 (with one or more probe(s) 122) and a radiometry system 130 (with a detection subsystem 140). The antenna temperature (the temperature of a particular probe 122 as detected by the radiometry system 130) $T_A$ can be a combination of an upper half-space (e.g., near-ambient) temperature ($T_U$), a probe 122 feed (e.g., surface 115) temperature $T_F$, and multiple lower half-space (e.g., tissue layer 120) temperatures ($T_{VN}$, where n=1, 2, 3 . . . ). Each component temperature can be associated with a corresponding weighting function (W). For example, the antenna temperature can be expressed as a weighted average of the temperature of the tissue layers (Equation 1):

$$T_A=T_UW_U+T_FW_F+T_{V1}W_{V1}+T_{V2}W_{V2}+T_{V3}W_{V3}$$

Thus, the layer temperatures can effectively be backed out from the measurement of the total power, observed as the $T_A$ measurement by the radiometer.

Figure 3:
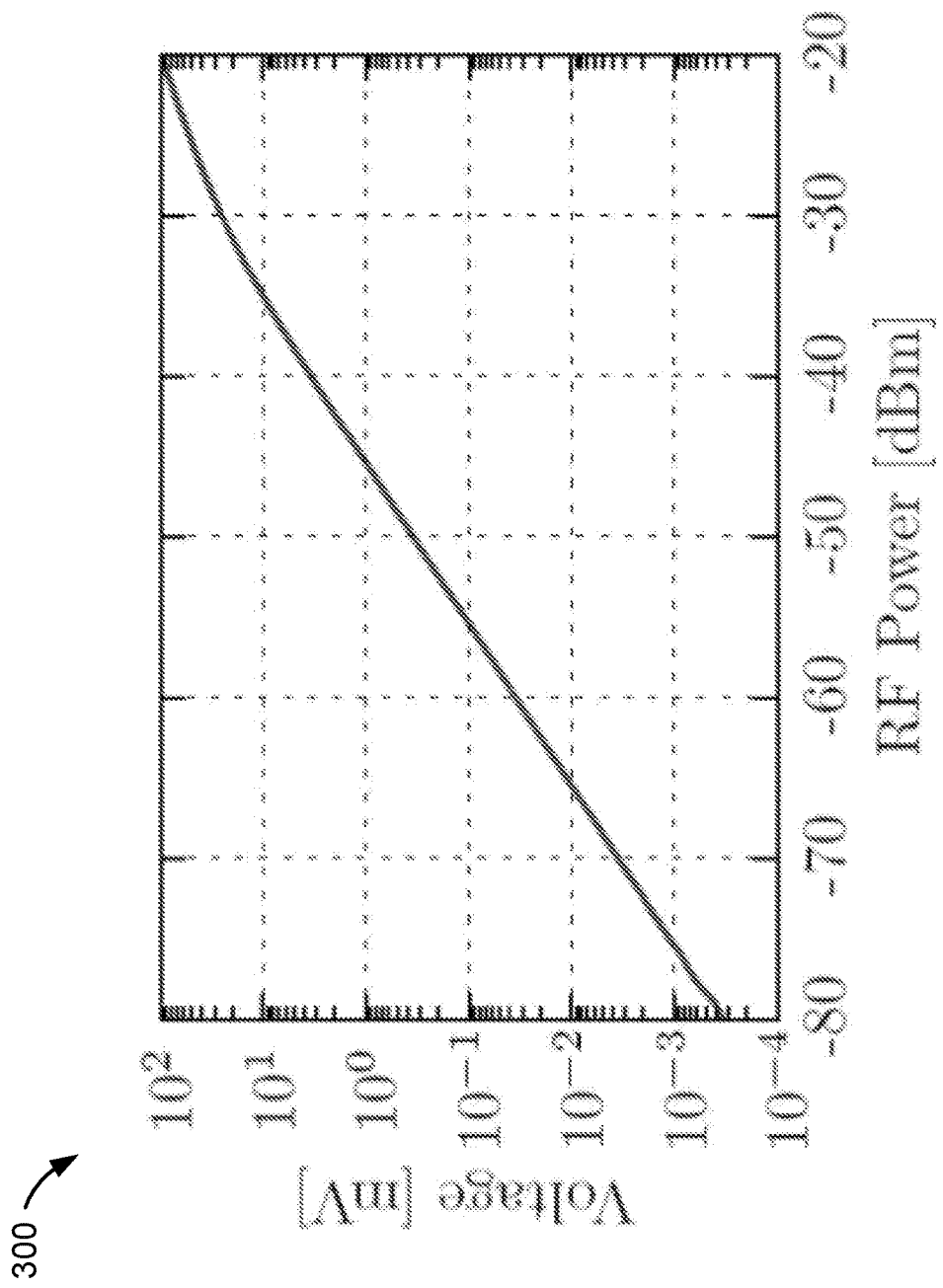
FIG. 3 shows a graph of an illustrative measured responsivity of a detection subsystem of a radiometry system, such as the one shown in FIG. 1.

FIG. 3 shows a graph 300 of an illustrative measured responsivity of a detection subsystem 140 of a radiometry system 130, such as the one shown in FIG. 1. For example, the radiometry system 130 can include a square-law diode detector as its detector stage 138. The illustrative measured responsivity of such a square-law detector is shown in FIG. 3 as 25 mV/μW at 1.4 GHz. Another aspect of effective radiometry system 130 (receiver) design is proper determination of gain and receiver sensitivity requirements. The RF power can be calculated, using a 27-MHz bandwidth and normal body temperature of ≈310 K, as −99.4 dBm. Realizing a desired output voltage of 100 μV (e.g., to place input power within the square-law region of the detector) can involve 45 dB of gain. The radiometric resolution can be written as Equation 2:

$$\Delta T = \frac{T'_A + T_{rec}}{\sqrt{B_\tau}}$$

where $T'_A$ is the antenna temperature including the ohmic losses, $T_{rec}$ is the receiver temperature and $\tau$ is the integration time. For a resolution of 0.2 K, determining the required receiver temperature can involve assuming integration time, $\tau$=0.333 s. The corresponding noise figure can be NF=3 dB. With this information, parts can be selected to achieve appropriate gain and cascaded noise figures.

Figure 4:
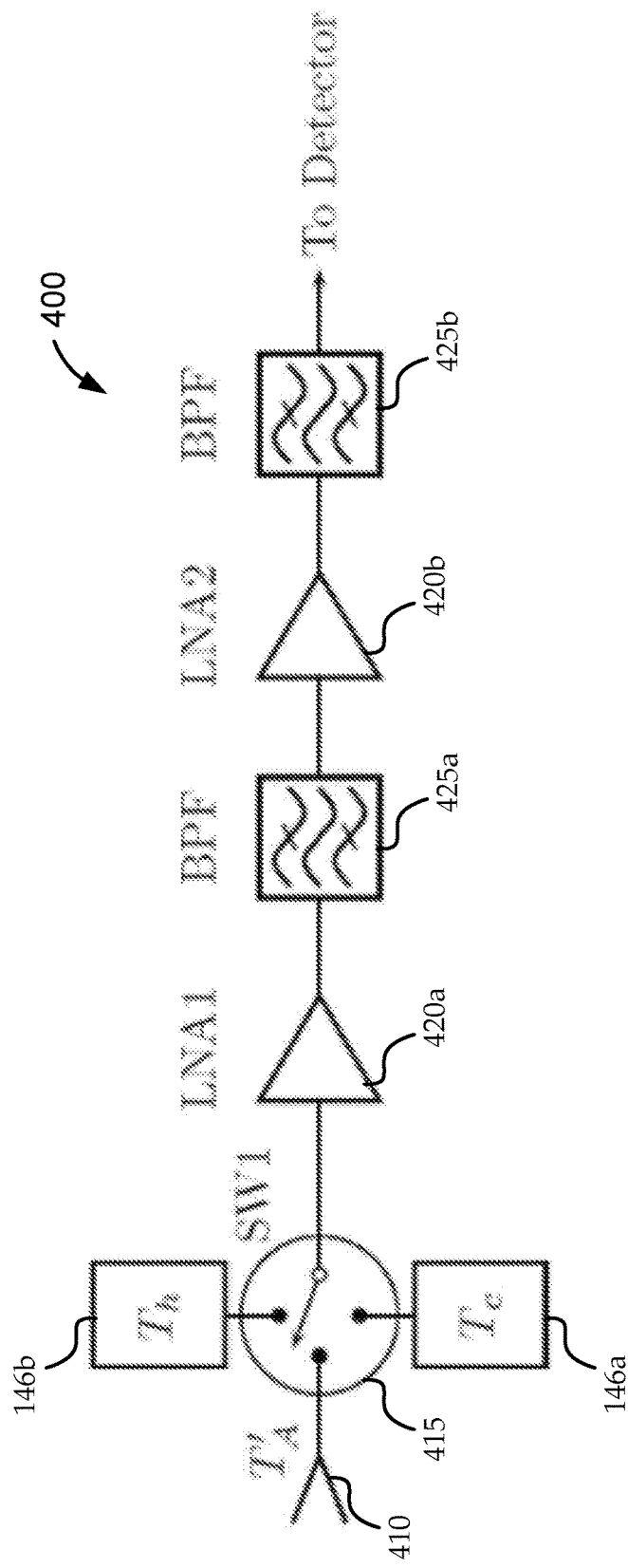
FIG. 4 shows an illustrative circuit block diagram of an embodiment of an input (probe-side) portion of a radiometry system, according to various embodiments.

FIG. 4 shows an illustrative circuit block diagram 400 of an embodiment of an input (probe-side) portion of a radiometry system 130, according to various embodiments. The illustrated embodiment includes a signal path having two amplifier stages 134 and two filter stages 136. In particular, the architecture is illustrated as having a first LNA 420a, a first BPF 425a, a second LNA 420b, and a second BPF 425b. The input to the signal path can include a switch that can select between the probe antenna device 410 (e.g., a probe 122, shown as $T'_A$), a "hot" noise signal source ($T_h$) 146b (e.g., one of the calibration noise sources 146), and a cold noise signal source ($T_c$) 146a (e.g., another of the calibration noise sources 146). As described below, the hot and cold noise signal sources can be used for calibration (e.g., dynamic calibration during operation). As one example, a 1.4 GHz radiometer embodiment of FIG. 4 can be implemented with the following components:

| Element | Manufacturer | Part Number | G[dB] | NF[dB] |
|---|---|---|---|---|
| SW1 | Hittite | HMC345LP3 | −2 | 2 |
| LNA1 | Mini-Circuits | RAMP-33LN | 16.7 | 1 |
| BPF | Mini-Circuits | VBFZ-1400 | −2 | 2 |
| LNA2 | Mini-Circuits | TAMP | 34.9 | 0.6 |

Figure 5:
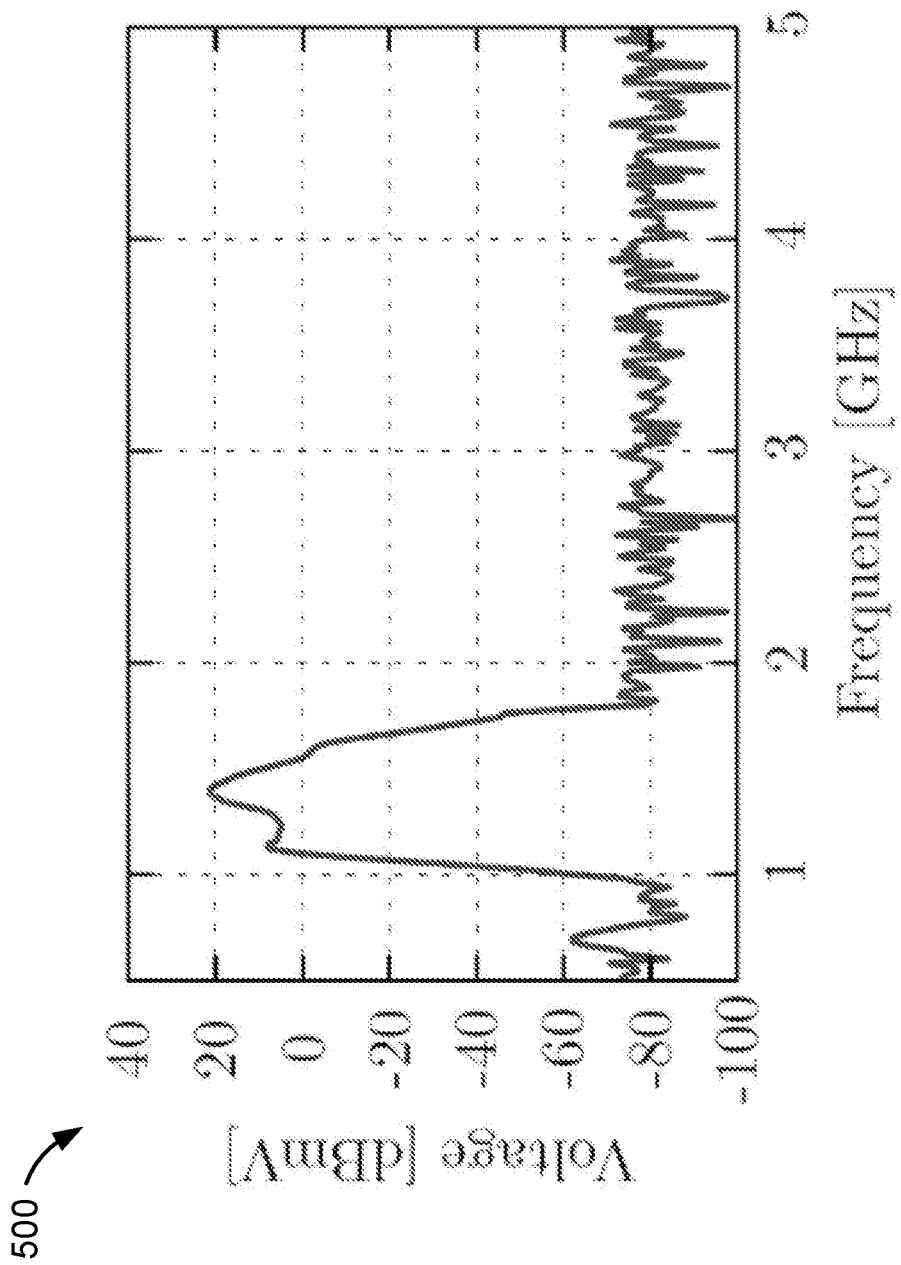
FIG. 5 shows a graph of an illustrative measured frequency response of a radiometry system, such as one having the circuit shown in FIG. 4.

FIG. 5 shows a graph 500 of an illustrative measured frequency response of a radiometry system 130, such as one having the circuit 400 shown in FIG. 4. The graph 500 shows an experimentally measured performance for an illustrative 1.4 GHz receiver over a range of RF input frequencies at an input power of −80 dBm. The same radiometry system 130 implementation also experimentally produced an output voltage of 127.6 μV for an input power of −100 dBm.

According to the above, the operation of embodiments described herein are based on black-body radiation and Plank's law. A probe 122 (e.g., a near-field antenna) is placed in intimate contact with the skin above the position where the temperature difference is sensed (e.g., at the surface 115 of a skin site 110 corresponding in position to the internal tissue site of interest). The probe 122 can receive band-limited noise, the power of which being proportional to the temperature, as detected by a radiometry system 130. The total detected power, together with a model of tissue layer thickness and electrical properties, can be used to compute temperature in a specific layer 120.

Though some radiometry system 130 designs are described above as operating at a particular frequency and receiver bandwidth, other values can be used for various applications and/or purposes. For example, selection of the operating frequency of the probe 122 can impact depth of penetration of the radiation through different tissue layer stacks (e.g., lower frequencies generally penetrate more deeply). Because the probe 122 operates is in the near field, standard skin-depth theory may not apply. Instead, the received signal can be proportional to the total received power from all the layers 120 under the probe. In addition to the frequency, operating bandwidth can be an important design consideration, as it can impact total power received (and therefore signal-to-noise ratio (SNR)), and radio-frequency interference (RFI). To mitigate the latter, some implementations can use narrow-band receivers traded with longer integration time (e.g., on the order of seconds, which can still be relatively short for monitoring temperature changes). Additionally, filters and amplifiers can be strategically cascaded within the radiometry system 130 architecture. Implementations of the probe 122 can be designed to operate in close proximity to the skin (e.g., planar or otherwise with appropriate skin contact design and means, adhesion or other placement means, etc.), and shielded from RFI. For example, a planar probe antenna implementation can be placed in contact with the skin and made with a substrate (e.g., a solid substrate, or a flexible substrate to allow better contact with the skin) that is impedance-matched to the skin and biocompatible. RFI shielding can be accomplished in some embodiments by designing the probe 122 to be a good receiver of near-field radiation through tissue, while being a poor receiver of external-field radiation. For example, some implementations of the probe 122 are designed to be small and to have an impedance that is closely matched to tissue, while being poorly matched to air. Some other implementations can be backed by a ground plane, such as in a patch or cavity-backed spiral probe antenna. For example, a planar probe antenna implementation can be RFI shielded with a ground plane and circuit on the back incorporated into a same substrate.

Some embodiments are designed to achieve desired vertical (depth) temperature resolution, spatial resolution, and/or other features. For example, some implementations use multiple frequencies to obtain depth temperature resolution. Some such implementations use multiple frequency probes 122 and/or radiometry systems 130 to obtain measurements with multiple frequencies. Other such implementations use a single probe 122 (and/or radiometry system 130) with a multi-band response, each for a different frequency. For example, some embodiments can concurrently record temperatures at different depths using multiple radiation frequencies. The temperature versus depth information can be used to more accurately derive core temperature, for example, by providing additional data for the determination of the weighting functions of the body tissue stack model, by helping to calibrate out effects from one or more layers, etc.

Some implementations can use multiple probes 122, operating at the same and/or different frequencies with one or more receivers, to obtain multiple measurements with spatial diversity. Such spatial diversity can provide various features, such as spatial resolution, thermal information from different locations on a body (e.g., concurrently), measurement redundancy (e.g., for verification, error detection, etc.), etc. Implementations can be carefully designed to achieve spatial resolution (e.g., appropriate focus, directionality, etc.), even though the probes 122 rely on near-field effects, and therefore cannot be designed with standard phased-array techniques.

Some implementations of the antenna probe 122 can include a multiple coaxial probes that allow for multiple frequencies, different reception patterns at a same frequency, etc. This can allow for multiple measurements at a same location in one probe 122, which can provides for solving for temperature in multiple tissue layers. While some embodiments can use multiple probes 122 and/or probe 122 frequencies, such embodiments often use of multiple probes 122 and/or probe 122 frequencies, which can increase the size of the device, increase power consumption of the device (e.g., thereby decreasing battery life, increasing heating of device components, etc.), increase electromagnetic interference caused and/or experienced by the device, etc. These and other factors can complicate (or even prevent) effective use of such designs in some wearable and other portable applications. Accordingly, for many applications, it can be desirable to obtain reliable core body temperature measurements from a single probe 122 and/or small measurement bandwidth. Achieving desired temperature depth resolution, spatial resolution, and/or other results in such applications can rely on effective calibration, which can be performed in a number of ways.

Calibration can be performed at multiple levels. For example, the instrumentation (e.g., the probe(s), the radiometer(s), etc.) can be calibrated generally prior to operation; during operation to compensate for dynamic changes; and/or before and/or during operation for a particular user. Some embodiments can calibrate the instrumentation generally prior to operation by using one or more body models, as described above. For example, mathematical and/or empirical (e.g., experimental) data can be used to model electric field magnitudes and/or other relevant information for one or more tissue layer models. Some such embodiments can use multiple models for different body types (e.g., older, younger, overweight, underweight, male, female, etc.), different physiological characteristics (e.g., layer thicknesses, compositions, electrophysiology, thermal characteristics, etc.), different operating frequencies, etc. One or more of the models can be stored in (or accessible to) the system (e.g., the signal processing system 150 of FIG. 1). As described above, such a tissue layer model can be used to back out a particular layer temperature (e.g., a core temperature) from a measurement of total power being radiated from the tissue layer stack.

Calibration of the instrumentation during operation can be implemented in some embodiments by integrating hot and cold noise sources into the receiver circuit, for example, as described with reference to FIG. 4. Some embodiments of the system (when properly calibrated) can manifest a substantially deterministic (e.g., linear) relationship between measured power and core body temperature. For example, a stored model can be used to obtain at least a "hot" point and a "cold" point, representing expected power measurements at a particular hot and cold temperature, respectively. If the response is sufficiently linear, the hot and cold points can be used to compute a slope, which can be used to mathematically relate any measured power to a corresponding core body temperature. During operation of the system, internal heating of components, electromagnetic interference, and/or other dynamic factors can affect the power measured by the probe 122 and/or detected by the radiometry system 130 even absent any change in core body temperature, which can impact the core body measurements (e.g., by shifting the hot and/or cold points). Accordingly, some embodiments can periodically switch the input of the radiometry system 130 from the actual probe assembly 120 to a hot and/or cold calibration noise source 146. Each signal can output a particular, known power level corresponding to a particular core body temperature, and the system (e.g., the signal processing system) can use measurements of the hot and/or cold signal to calibrate the instrumentation. For example, during operation the hot and/or cold points (e.g., and/or any other suitable number of points using additional signal sources) can be dynamically calibrated to preserve a reliable correspondence between power and temperature.

Some embodiments include additional calibration based on conduction. In addition to electromagnetic black-body radiation, which is received instantly (the radiation travels at the speed of light in the tissues), there is also thermal conduction from the warmer internal layers to the skin, which can impact measurement of the radiated temperature by the radiometry system 130. The temperature change due to thermal conduction can be measured by a surface temperature probe, such as an inexpensive thermocouple sensor (e.g., the thermocouple(s) 124 of FIG. 1). Accordingly, some embodiments use the conductive temperature measurement to calibrate out such effects as part of the radiometry system 130 temperature retrieval. For example, by incorporating one or more radiometry measurements with one or more co-located surface temperature measurements (e.g., taken by a different technique, such as a thermistor, thermocouple, IR, etc.), the combination of surface and radiometry measurements can be used to calibrate the radiometry system 130, calculate the temperatures of multiple tissue layers, eliminate error caused by heat conduction through the layers 120, etc. Other embodiments can use the conductive measurements as additional data for core temperature retrieval. For example, some models can include surface temperature as a variable, which can be obtained and/or verified by the conductive surface measurement. Additionally or alternatively, other embodiments can use the conductive measurements as an additional source of thermal information for diagnosis and/or other purposes. For example, certain physiological changes (e.g., characteristic of normal physiological response, of abnormal physiological response, of physiological danger, of a disorder, etc.) may manifest as a particular relationship (or change in relationship) between the measure core temperature and the measured surface temperature in a particular body site.

In some embodiments, the conduction information can be used as part of the so-called "inverse problem" of retrieving the core body temperature. As described above, the inverse problem can involve backing out the temperature of internal tissue layers from a total power measurement based on weighting functions. In some embodiments, the inverse problem further involves adjusting the weighting functions based on one or more types of information. For example, when internal tissue layers change temperature, the black-body radiation effects are substantially immediate and the corresponding radiation information is communicated through tissue to the radiometer substantially in real time (i.e., at close to the speed of light). In contrast, temperature changes due to conduction take time to conduct through tissue layers, so that any resulting conductive changes in surface temperature are reflected much more slowly. Some embodiments can use conduction information (e.g., in post-processing) at a particular time to adjust weighting functions applied to radiometry information from a previous time, thereby impacting the inverse problem.

Some embodiments include additional calibration of the system to one or more particular users. Some such embodiments can use time-domain-reflectometry (e.g., using the reflectometer(s) 126 of FIG. 1) to obtain active measurements of tissue layer depths for one or more specific location on a body. Such measurements can then be compared against one or more stored tissue layer models to select an appropriate model (e.g., a pre-calibration model that most closely matches the reflectometry measurement), to tune or otherwise adapt a stored model, etc. As described above, the measured or assumed tissue layer thicknesses can yield a tissue layer model, and the modeled layers can be associated with weighting functions determined from full-wave electromagnetic simulations, from empirical measurements, and/or from any other suitable source. The weighting functions, in combination with estimation algorithms and power measurement data, can be used to retrieve one or more internal temperature profiles.

For the sake of added disclosure, implementations of embodiments described herein can be experimentally verified. For example, two probe designs are analyzed for operation in the quiet 1.4 GHz band: a folded dipole design, and a circular patch design. The dipole design can be fed by a tapered balun and fabricated on Rogers 4350B ($\varepsilon_r$=3.66) substrate. Experimentally, the return loss is shown to be greater than 20 dB in the band of interest. The patch design can be fabricated on a Rogers 6010 ($\varepsilon_r$=10.2) substrate with a superstrate of the same material which reduces the sensitivity of the probe to the surrounding media. This can be advantageous for complex and variable tissue thicknesses in human bodies. The patch additionally has a ground plane and can have a narrower bandwidth, which can help reduce RFI. Experimentally, the return loss is for the patch design is shown to be better than 20 dB in the frequency band of interest. As described above, interference mitigation techniques, including shielding and active interference cancellation, can be included in some implementations. For purposes of experimental validation, two planar compact probe antennas can be positioned on the surface of a half-space water phantom and placed in an anechoic chamber to eliminate unknown interference. A hot and cold noise source calibration can be performed with an Agilent 346A noise source a room-temperature microwave load, respectively. The temperature of the load can be measured with a thermocouple connected to a PicoTech.0 TC-08 data logger. The calibration can be performed every second with an equal dwell time on each of the standards and the probe, which is measuring an unknown temperature. The received data at the output of the detector can then be processed using an estimation algorithm. A thermocouple sensor can be placed in the water bath, which can be heated to 40° C. when the patch is used, and to 35° C. when the dipole probe is used. Results from such an experimental setup can show that estimated temperatures from both probes tend to follow the thermocouple measurement to within 0.7K as the water phantom cools to below 30° C. in 55 minutes. In each case, a fixed bias in the data can be calibrated out, and the bias is typically larger for the patch probe.

Figure 6:
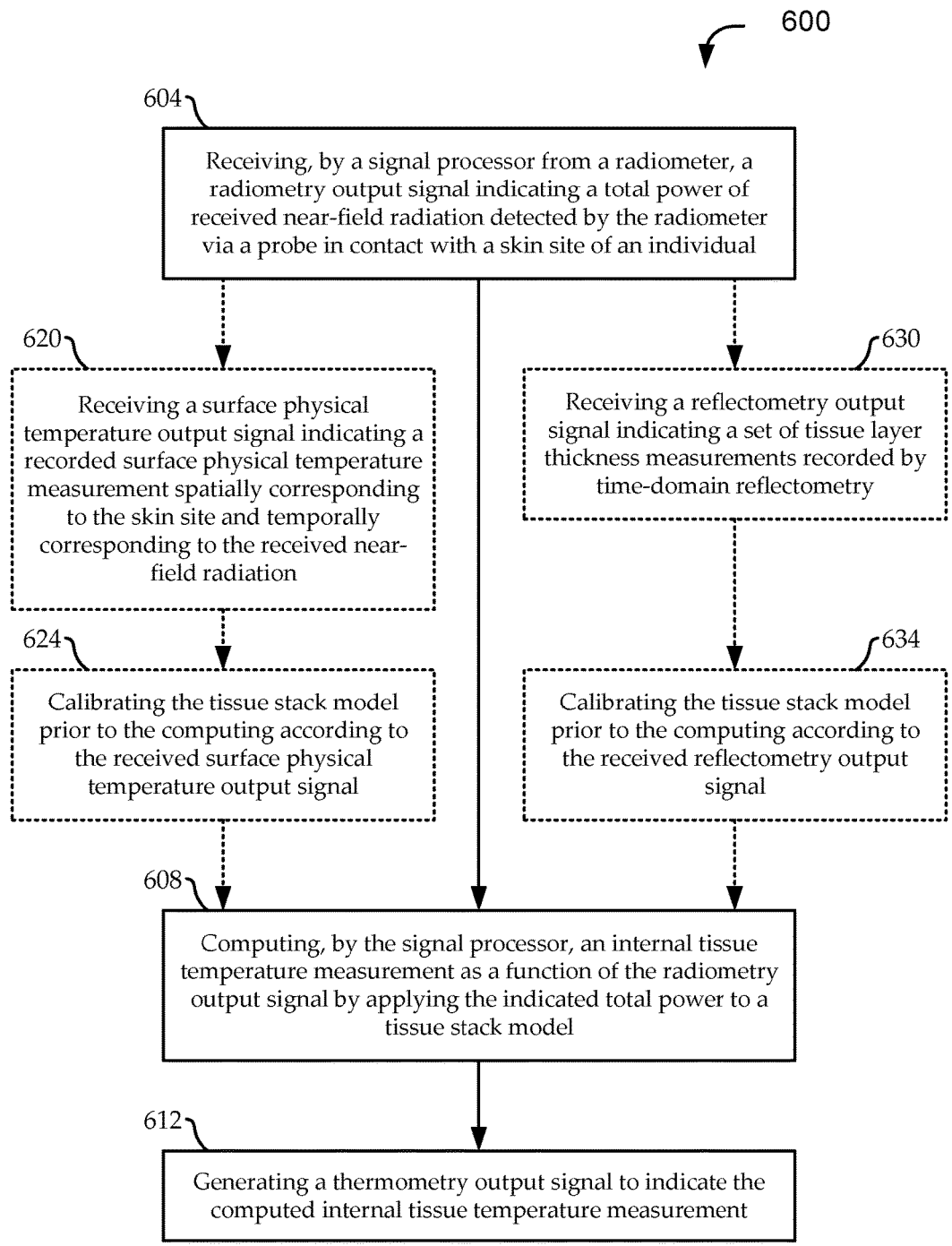
FIG. 6 shows a flow diagram of an illustrative method for retrieving internal body temperature by microwave thermometry, according to various embodiments.

FIG. 6 shows a flow diagram of an illustrative method 600 for retrieving internal body temperature by microwave thermometry, according to various embodiments. Embodiments of the method 600 begin at stage 604 by receiving a radiometry output signal indicating a total power of received near-field radiation. The receiving can be by a signal processor (e.g., signal processing system 150) from a radiometer (e.g., radiometry system 130), and the total power of received near-field radiation can be detected by the radiometer via a probe (e.g., probe assembly 120) in contact with a skin site of an individual. At stage 608, embodiments can compute (e.g., by the signal processor) an internal tissue temperature measurement as a function of the radiometry output signal by applying the indicated total power to a tissue stack model. As described herein, the tissue stack model can characterize the skin site according to a set of weighting functions, and each weighting function can correspond at least to electromagnetic characteristics of an associated tissue layer of the tissue stack model. At stage 612, embodiments can generate a thermometry output signal to indicate the computed internal tissue temperature measurement.

Various embodiments can include additional stages. Some embodiments, at stage 620, can receive a surface physical temperature output signal indicating a recorded surface physical temperature measurement (e.g., from a thermocouple, or the like) spatially corresponding to the skin site and temporally corresponding to the received near-field radiation. Such embodiments, at stage 624, can calibrate the tissue stack model prior to the computing at stage 608, according to the received surface physical temperature output signal. Other embodiments, at stage 630, can receive a reflectometry output signal (e.g., from a reflectometer) indicating a set of tissue layer thickness measurements recorded by time-domain reflectometry. Such embodiments, at stage 634, can calibrate the tissue stack model prior to the computing according to the received reflectometry output signal.

The various techniques can be implemented with any suitable hardware and/or software component(s) and/or module(s), including, but not limited to circuits, application specific integrated circuits (ASICs), general purpose processors, digital signal processors (DSPs), field programmable gate arrays (FPGAs), programmable logic devices (PLD), discrete gates, transistor logic devices, discrete hardware components, or combinations thereof. For example, steps of methods or algorithms, or other functionality described in connection with embodiments, can be embodied directly in hardware, in a software module executed by a processor, or in a combination of the two. A software module may reside in any form of tangible storage medium. Some examples of storage media that may be used include random access memory (RAM), read only memory (ROM), flash memory, EPROM memory, EEPROM memory, registers, a hard disk, a removable disk, a CD-ROM and so forth. A storage medium may be coupled to a processor such that the processor can read information from, and write information to, the storage medium. In the alternative, the storage medium may be integral to the processor. A software module may be a single instruction, or many instructions, and may be distributed over several different code segments, among different programs, and across multiple storage media. Thus, a computer program product may perform operations presented herein. For example, such a computer program product may be a computer readable tangible medium having instructions tangibly stored (and/or encoded) thereon, the instructions being executable by one or more processors to perform the operations described herein. The computer program product may include packaging material. Software or instructions may also be transmitted over a transmission medium. For example, software may be transmitted from a website, server, or other remote source using a transmission medium such as a coaxial cable, fiber optic cable, twisted pair, digital subscriber line (DSL), or wireless technology such as infrared, radio, or microwave.

The methods disclosed herein include one or more actions for achieving the described method. The method and/or actions can be interchanged with one another without departing from the scope of the claims. In other words, unless a specific order of actions is specified, the order and/or use of specific actions can be modified without departing from the scope of the claims. The various operations of methods and functions of certain system components described above can be performed by any suitable means capable of performing the corresponding functions.

Other examples and implementations are within the scope and spirit of the disclosure and appended claims. For example, features implementing functions can also be physically located at various positions, including being distributed such that portions of functions are implemented at different physical locations. Also, as used herein, including in the claims, "or" as used in a list of items prefaced by "at least one of" indicates a disjunctive list such that, for example, a list of "at least one of A, B, or C" means A or B or C or AB or AC or BC or ABC (i.e., A and B and C). Further, the term "exemplary" does not mean that the described example is preferred or better than other examples.

Various changes, substitutions, and alterations to the techniques described herein can be made without departing from the technology of the teachings as defined by the appended claims. Moreover, the scope of the disclosure and claims is not limited to the particular aspects of the process, machine, manufacture, composition of matter, means, methods, and actions described above. Processes, machines, manufacture, compositions of matter, means, methods, or actions, presently existing or later to be developed, that perform substantially the same function or achieve substantially the same result as the corresponding aspects described herein can be utilized. Accordingly, the appended claims include within their scope such processes, machines, manufacture, compositions of matter, means, methods, or actions.

What is claimed is:

1. A microwave thermometry system comprising:
   a wearable probe assembly that operates, when placed on a skin site of an individual, to receive near-field radiation at the skin site;
   a radiometer coupled with the probe assembly to detect a total power of the received near-field radiation; and
   a signal processing system coupled with the radiometer to convert the detected total power to an internal tissue temperature measurement as a function of applying the detected total power to a tissue stack model,
   the tissue stack model characterizing the skin site according to a set of weighting functions, each weighting function corresponding at least to electromagnetic characteristics of an associated tissue layer of the tissue stack model.

2. The system of claim 1, wherein the probe assembly operates to receive the near-field radiation at the skin site at a frequency band tuned to correspond to a predetermined tissue penetration depth.

3. The system of claim 1, wherein the probe assembly comprises a plurality of wearable probes that operate concurrently and are arranged to receive the near-field radiation at the skin site with spatial diversity.

4. The system of claim 1, wherein the probe assembly comprises:
   a patch probe impedance-matched to the skin site.

5. The system of claim 1, further comprising:
   a housing having the probe assembly, the radiometer, and a wireless transmitter disposed therein,
   wherein the signal processing system is separate from the housing and in wireless communication with the wireless transmitter.

6. The system of claim 1, further comprising:
   a data store coupled with the radiometer to store the detected total power at each of a plurality of times over a detection window,
   wherein the signal processing system operates to convert the detected total power to the internal tissue temperature measurement at each of the plurality of times by, for each time:
   accessing the stored detected total power for the time from the data store; and
   applying the accessed detected total power to the tissue stack model.

7. The system of claim 1, wherein the signal processing system comprises:
   a processor coupled with the radiometer; and
   a memory having, stored thereon, the tissue stack model, and instructions, which when executed, cause the processor to convert the detected total power to the internal tissue temperature measurement as a function of applying the detected total power to the tissue stack model.

8. The system of claim 1, wherein the probe assembly comprises:
   a first probe that operates to receive the near-field radiation at the skin site at a first frequency band tuned to correspond to a predetermined first tissue penetration depth associated with a first tissue layer of the tissue stack model; and
   a second probe that operates to receive the near-field radiation at the skin site at a second frequency band tuned to correspond to a predetermined second tissue penetration depth associated with a second tissue layer of the tissue stack model.

9. The system of claim 8, wherein the first and second probes operate concurrently.

10. The system of claim 1, wherein the probe assembly further comprises:
    a thermocouple that operates to retrieve a surface physical temperature measurement at the skin site,
    wherein the signal processing system operates to convert the detected total power to the internal tissue temperature measurement further according to the surface physical temperature measurement.

11. The system of claim 10, wherein:
    the signal processing system operates to convert the detected total power to the internal tissue temperature measurement for a first time by applying the detected total power to a tissue stack model having values for the set of weighting functions at the first time adjusted according to the surface physical temperature measurement for a second time that is subsequent to the first time.

12. The system of claim 1, further comprising:
    a reflectometer that operates to retrieve a set of tissue layer thickness measurements according to time-domain reflectometry,
    wherein the signal processing system further operates to compute the tissue stack model according to the set of tissue layer thickness measurements prior to applying the detected total power to the tissue stack model.

13. The system of claim 12, wherein the signal processing system operates to compute the tissue stack model by calibrating a stored tissue stack model according to the set of tissue layer thickness measurements.

14. The system of claim 12, wherein the signal processing system operates to compute the tissue stack model by selecting one of a plurality of stored tissue stack models that most closely corresponds to the set of tissue layer thickness measurements.

15. The system of claim 1, wherein the radiometer comprises:
- a detector that operates to detect the total power of the received near-field radiation;
- a noise source that outputs a predetermined power corresponding to a predetermined temperature; and
- a switch that operates to selectively couple the detector with either the probe assembly or the noise source,
- wherein the signal processing system further operates to calibrate the radiometer by compensating for a gain offset that is determined, while the switch couples the detector with the noise source, according to comparing the predetermined temperature with the internal tissue temperature measurement converted from the predetermined power.

16. The system of claim 15, wherein the noise source comprises:
- a hot noise source that outputs a first predetermined power corresponding to a predetermined hot temperature; and
- a cold noise source that outputs a second predetermined power corresponding to a predetermined cold temperature.

17. The system of claim 16, wherein the signal processing system operates to:
- compute a hot measurement while the switch couples the detector with the hot noise source;
- compute a cold measurement while the switch couples the detector with the cold noise source; and
- calibrate the radiometer by fitting a correlation function to the hot measurement and the cold measurement and de-skewing the detected total power according to the correlation function.

* * * * *